United States Patent [19]

Chen et al.

[11] 4,148,835

[45] Apr. 10, 1979

[54] HYDROCARBON MANUFACTURE FROM ALCOHOLS

[75] Inventors: Nai Y. Chen, Titusville, N.J.; William J. Reagan, Yardley, Pa.

[73] Assignee: Mobil Oil Corporation, New York, N.Y.

[21] Appl. No.: 896,267

[22] Filed: Apr. 14, 1978

[51] Int. Cl.$^2$ .............................................. C07C 1/20
[52] U.S. Cl. ................................................... 260/682
[58] Field of Search ....................................... 260/682

[56] References Cited

U.S. PATENT DOCUMENTS 4,025,571  5/1977  Lago ................................... 260/682

Primary Examiner—C. Davis
Attorney, Agent, or Firm—Charles A. Huggett; Raymond W. Barclay; Claude E. Setliff

[57] ABSTRACT

A catalytic process is provided for converting a feed containing a $C_1$-$C_4$ monohydric alcohol by contact of said alcohol, under conversion conditions, with a catalyst comprising a crystalline aluminosilicate zeolite having a crystal size of at least about 1 micron, a silica to alumina ratio of at least about 12 and a constraint index, as hereinafter defined, within the approximate range of 1 to 12. The zeolite contains a Group 2B and a Group 8 metal or metal compound plus magnesium, either per se or in compound form.

14 Claims, No Drawings

HYDROCARBON MANUFACTURE FROM ALCOHOLS

BACKGROUND OF THE INVENTION

1. Field of the Invention

This invention relates to a process for the conversion of low molecular weight monohydric alcohols to olefinic hydrocarbons in the presence of a specified crystalline aluminosilicate zeolite catalyst characterized by a crystal size of at least about 1 micron.

2. Description of the Prior Art

A remarkable growth in the production of synthetic fibers, plastics and rubber has taken place in recent decades. This growth, to a very large extent, has been supported and encouraged by an expanding supply of inexpensive petrochemical raw materials such as ethylene, benzene, toluene and xylenes.

Increasing demand for olefins, e.g. $C_2$-$C_3$ olefins has, from time to time, led to periods of shortage, either due to a diminished supply of suitable feedstocks or to limited processing capacity. In any even, it is desirable to provide efficient means for converting raw materials other than petroleum to olefins.

Understandably, there has been considerable effort made to find new ways to produce certain olefin hydrocarbons. For example, U.S. Pat. No. 4,025,571 discloses the conversion of a feed of alcohols, ethers and mixtures thereof to hydrocarbons rich in $C_2$— and $C_3$ hydrocarbons and certain aromatics by passing the feed over the specified zeolites.

SUMMARY OF THE INVENTION

In accordance with the present invention, there has been discovered a process which produces valuable light olefinic hydrocarbons with high selectivity for total olefin production, especially ethylene production. The present process involves conversion of a feed containing a lower monohydric alcohol having up to four carbon atoms by contact at elevated temperatures with a catalyst comprising a crystalline aluminosilicate zeolite having a crystal size of at least about 1 micron, usually in the approximately range of 1–20 microns and preferably 1–6 microns. The crystalline aluminosilicate zeolite is essentially characterized by a silica to alumina ratio of at least about 12, a constant index within the approximate range of 1 to 12 and the presence therein of a Group 2B and a Group 8 metal or metal compound and magnesium or its oxide or sulfide, to yield a reaction product mixture comprising light olefins and recovering these hydrocarbons.

DESCRIPTION OF SPECIFIC EMBODIMENTS

It is contemplated that a feed comprising any monohydric alcohol having from 1 to 4 carbon atoms may be used as feed to the process of this invention. Thus, methanol, ethanol, n-propanol, isopropanol, n-butanol, sec-butanol and isobutanol may be used either alone or in admixture with one another. The particularly preferred feed is methanol.

In accordance with the present invention, such feed is brought into contact, under conversion conditions, with a catalyst comprising a crystalline aluminosilicate zeolite having a crystal size of at least about 1 micron, a silica to alumina ratio of at least about 12 and a constraint index within the approximate range of 1 to 12, and having zinc, palladium and magnesium oxide associated therewith.

The zeolites herein described are members of a class of zeolites exhibiting some unusual properties. These zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina ratio of at least about 12; and a structure providing a constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolite, after activation, acquire an intracrystalline sorption capability for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed a 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F. with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Pat. No. 4,046,859.

The synthetic ZSM-35 zeolite possesses a definite distinguishing crystalline structure whose x-ray diffraction pattern shows substantially the significant lines set forth in Table II. It is observed that this x-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong - Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination of 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ OH−/SiO₂ | 0.2–1.0 | 0.3–0.9 |
| OH−/SiO₂ | 0.05–0.5 | 0.07–0.49 |
| H₂O/OH− | 41–500 | 100–250 |
| SiO₂/Al₂O₃ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of $OH^-$ is calculated only from the inorganic sources of alkali without any organic base contribution.) Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

The crystals of this invention may be in the hydrogen form, but they will contain a Group 2B metal, such as zinc, a Group 8 metal, such as palladium and magnesium. It will be understood that "metal" includes also its compound form, especially the oxide or the sulfide. It is desirable to calcine the catalyst after base exchange.

In a preferred aspect of this invention, the catalysts hereof are selected as those having a crystal framework density, in the dry hydrogen form, of not substantially below about 1.6 grams per cubic centimeter. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April, 1967," published by the Society of Chemical Industry, London, 1968. When the crystal structure is unknown, the crystal framework density may be determined by classical pyknometer techniques. For example, it may be determined by immersing the dry hydrogen from of the zeolite in an organic solvent which is not sorbed. by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The crystal size of the synthesized zeolite has been found to be an important factor affecting the desired conversion of the described alcohol and/or ether charge stock to low molecular weight olefins and paraxylene. The crystal size of the above-described crystalline aluminosilicate zeolite employed in the process of the invention is at least about 1 micron, being in the approximate range of 1–20 microns and particularly in the range of 1–6 microns. With the use of crystals within such size range, distinctly higher selectivity for production of the desired $C_2$–$C_3$ olefins and paraxylene has been observed as compared with comparable use of smaller size crystals.

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 0.1 percent by weight may be used.

The preferred catalyst will contain from about 0.1% to about 10%, preferably about 1% to about 5% by weight of the Group 2B component, of, as for example, zinc, about 0.1% to about 5%, preferably about 0.5% to about 2% by weight of the Group 8 component, for example, palladium and about 0.1% to about 30%, preferably 5% to about 15% by weight of the magnesium component. These concentrations apply whether they concern the metal per se or its compound form.

It may be desirable in some instances to incorporate the zeolite in another material resistant to the temperatures and other conditions employed in the conversion process. Such matrix materials are to be distinguished from the aforenoted inert diluents and include synthetic or naturally occurring substances as well as inorganic materials such as clay, alumina or other metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw states as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportion of finely divided zeolite and inorganic oxide gel matrix may vary widely with the zeolite content ranging from between 1 to about 99 percent by weight and more usually in the range of about 5 to about 80 percent by weight of the composite. In the process of this invention, the feed consisting essentially of one or more of the alcohols is contacted with the above described catalyst bed at a temperature of about 500° F. to about 950° F. and preferably about 600° F. to about 850° F.; a contact time equivalent to or the same as a weight hourly space velocity (WHSV) of about 1 to about 100 preferably about 2 to about 40, it being understood that WHSV signifies pounds of feed per pound of zeolite per hour; and at an absolute pressure of about 0.2 to about 50 atmospheres, preferably between about 1 and about 30 atmospheres.

The reaction product effluent from the process of the invention contains steam and a hydrocarbon mixture particularly rich in the light olefins, ethylene and propylene with some aromatic hydrocarbons with high selectivity for paraxylene. Generally, a major fraction of the total olefins, calculated on a mol basis, is ethylene plus propylene. The predominant aromatic hydrocarbons are monocyclic hydrocarbons, notably $C_8$ and $C_9+$ aromatics with a high proportion of paraxylene. Thus, the predominant hydrocarbons are all valuable petrochemicals. The steam and hydrocarbons are separated from one another by methods well known in the art.

Catalyst deactivated by coke deposited during the process may be regenerated by calcining in an oxygen-containing atmosphere, e.g. air, at an elevated temperature within the approximate range of 600° F. to 1200° F. for a period of between about 1 and about 30 hours.

The following examples will serve to illustrate the process of this invention without limiting the same:

Catalyst Preparation

ZSM-5C was made conventionally using the tetrapropylammonium and sodium cations. It was calcined and ion exchanged with the ammonium cation to yield the $NH_4$ZSM-5C utilized as described hereinafter.

Eleven grams of this $NH_4$ZSM-5C was calcined for 2 hours at 1000° F., 300 ml air flow. Then 2.63 g of $Zn(NO_3)_2 \cdot 6H_2O$ was added to 16 ml of water and the calcined catalyst was added thereto with stirring. The material was dried at 2 hours at 266° F. and was then calcined for 2 hours at 1000° F. in air.

Palladium chloride, 0.095 g., was dissolved in concentrated ammonium hydroxide and this solution was diluted to 18 ml. with hot water. The ZnZSM-5C was added with stirring. After completion of the impregnation, the ZnPdZSM-5 was dried for 2 hours at 266° F. and then was calcined for 2 hours at 1000° F.

To 10 ml. of water was added 1.85 g. of magnesium acetate and this solution was added to the ZnPdZSM-5C, which was 40/60 mesh. The excess water was evaporated under a heat lamp and the product was calcined for 17 hours at 572° F. and at 896° F. for 4 hours.

The product, ZnPdMgOZSM-5C, contained 0.5% palladium, 4.5% zinc and 10% magnesium oxide.

The conversion reactions were carried out in a vertically-mounted vycor microreactor, heated by a low heat capacity resistance furnace. The catalyst (40-60 mesh) was centered between alyers of pyrex chips. The feed, 20% wt. % methanol in water was pumped upflow over the catalyst bed. The reactor effluent passed through heat traced lines to a heated sample valve mounted on an HP 5750 gas chromatograph.

It will be understood that the feed may comprise the $C_1$–$C_4$ alkanol alone, or admixed with water or admixed with corresponding ethers, i.e., those containing a total of 2-8 carbon atoms. The reactor effluent was analyzed on a 12 ft. ⅛" column packed with n-octane on Porosil "C". The gas chromatograph program consisted of a five minute initial hold at room temperature, followed by a programmed heating rate of 15° C./minute to 160° C. and final hold. Sensitivity factors for hydrocarbon components were taken as unity, for dimethylether 3.0 and for methanol 3.6. Conversion was calculated on the basis of the $CH_2$ content of methanol feed. The hydrogen, carbon monoxide and carbon dioxide content of the effluent gas stream was monitored qualitatively by periodic sampling and gas chromatograph analysis with the HP refinery gas analyzer.

The conversion reactions can be run at from about 400° F. to about 1000° F. to about 1000° F., preferably about 500° to 700° F., at an LHSV of from about 0.1 to about 10, preferably about 0.5 to 3 and at a pressure of from about 0.5 to about 20 atmospheres, preferably about 1 to 5 atmospheres.

A representative listing of the hydrocarbon product distribution for the magnesium oxide modified catalyst is presented in Table 1.

TABLE 1

| Product Composition Methanol Conversion Studies Pd, Zn, MgO ZSM-5C | | | | |
|---|---|---|---|---|
| | Hydrocarbon Composition, wt. % | | | |
| Product | 1 | 2 | 3 | 4 |
| methane | 7.8 | 0.2 | 0.3 | 0.4 |
| ethane | 1.0 | 0.2 | 0.5 | 0.3 |
| ethylene | 53.4 | 45.9 | 43.5 | 50.6 |

TABLE 1-continued

Product Composition
Methanol Conversion Studies
Pd, Zn, MgO ZSM-5C

| Product | Hydrocarbon Composition, wt. % | | | |
|---|---|---|---|---|
| | 1 | 2 | 3 | 4 |
| propane | 2.6 | 2.4 | 3.7 | 1.9 |
| propylene | 16.0 | 27.4 | 24.9 | 25.6 |
| $C_4$ olefins | 2.6 | 5.1 | 8.0 | 5.2 |
| $C_4$ paraffins | 2.6 | 6.0 | 3.7 | 7.9 |
| $C_5^+$ | 1.6 | 0.9 | 3.6 | 0.9 |
| aromatics | 12.4 | 11.9 | 11.8 | 7.2 |
| aromatics/$C_5^+$ | 88.6 | 93.0 | 76.6 | 88.9 |
| total olefins | 72.0 | 78.4 | 76.4 | 81.4 |
| conversion ($CH_2$ basis) | 27.6 | 41.9 | 71.1 | 22.4 |

Run conditions:
Sample 1; 707° F., T.O.S.
26.0 hrs. initial, 1.1 LHSV.
Sample 2; 564° F., T.O.S.
21.0 hrs. after 2nd regeneration, 1.4 LHSV.
Sample 3; 581° F., T.O.S.
21.0 hrs. after 3rd regeneration, 1.2 LHSV.
Sample 4; 554° F., T.O.S.
28.0 hrs., after 3rd regeneration, 1.2 LHSV.

With methanol as the feed, it has been found that to get the maximum ethylene yield, the zinc, palladium, and magnesium oxide must be added to the zeolite in a specific order as described herein above, i.e., by adding zinc, palladium, and magnesium oxide, in that order.

We claim:

1. A process for producing hydrocarbons which comprises contacting, under conversion conditions a charge comprising a $C_1$-$C_4$ monohydric alcohol with a catalyst comprising a crystalline aluminosilicate zeolite having a crystal size of at least 1 micron, a silica-to-alumina ratio of at least about 12, a constraint index of about 1 to 12 and having associated therewith a Group 2B component, a Group 8 component and magnesium.

2. The process of claim 1 wherein the charge is alcohol, a mixture of alcohol and water or a mixture of alcohol and the corresponding ether.

3. The process of claim 2 wherein the charge is an alcohol.

4. The process of claim 3 wherein the alcohol is methanol.

5. The process of claim 2 wherein the charge is a mixture of alcohol and water.

6. The process of claim 1 wherein the crystal size is within the range of from 1 to 20.

7. The process of claim 6 wherein the range is from 1 to 6.

8. The process of claim 1 wherein the Group 2B component is zinc.

9. The process of claim 1 wherein the Group 8 component is palladium.

10. The process of claim 1 wherein the catalyst used comprises zinc, palladium and magnesium.

11. The process of claim 10 wherein the zeolite is ZSM-5.

12. The process of claim 10 wherein the catalyst comprises from about 0.1 to about 10% by weight of the zinc component from about 1 to about 5% by weight of the palladium comonent and from about 0.1 to about 30% by weight of the magnesium component.

13. The process of claim 4 wherein the catalyst is a zinc, palladium, magnesium oxide-containing zeolite, said zinc, palladium, and magnesium oxide have been added to said zeolite in that order.

14. The process of claim 1 wherein the hydrocarbon produced contains a predominant amount of ethylene.

* * * * *

UNITED STATES PATENT AND TRADEMARK OFFICE
CERTIFICATE OF CORRECTION

PATENT NO. : 4,148,835
DATED : April 10, 1979
INVENTOR(S) : Nai Y. Chen and William J. Regan It is certified that error appears in the above-identified patent and that said Letters Patent are hereby corrected as shown below:

Column 5, line 56, "crystals" should read --catalysts--.

Column 10, line 29, "comonent" should read --component--.

Signed and Sealed this

Twenty-first Day of August 1979

[SEAL]

Attest:

Attesting Officer

LUTRELLE F. PARKER
Acting Commissioner of Patents and Trademarks